United States Patent [19]
Fesus et al.

[11] Patent Number: 6,063,797
[45] Date of Patent: May 16, 2000

[54] γ-RAR ANTAGONIST LIGAND OR α-RAR AGONIST LIGAND AS AN APOPTOSIS INHIBITOR

[75] Inventors: Laszlo Fesus; Zsuzsa Szondy, both of Debrecen, Hungary; Uwe Reichert, Pont-du-Loup, France

[73] Assignee: C.I.R.D. Galderma, Valbonne, France

[21] Appl. No.: 09/051,397

[22] PCT Filed: Oct. 8, 1996

[86] PCT No.: PCT/FR96/01569

§ 371 Date: Jul. 15, 1998

§ 102(e) Date: Jul. 15, 1998

[87] PCT Pub. No.: WO97/13506

PCT Pub. Date: Apr. 17, 1997

[30] Foreign Application Priority Data

Oct. 11, 1995 [FR] France .................................. 95 11946

[51] Int. Cl.$^7$ .................................................. A01N 37/12
[52] U.S. Cl. .................... 514/356; 514/510; 514/511; 514/533; 514/534; 514/535; 514/537; 514/562; 514/563; 514/564; 514/566; 514/567; 514/569; 514/570; 514/574; 514/577; 514/878; 514/893; 514/903
[58] Field of Search ..................... 518/356, 510, 518/511, 533, 878, 534, 893, 535, 903, 537, 562, 563, 564, 566, 567, 569, 570, 574, 577

[56] References Cited

U.S. PATENT DOCUMENTS

| | | | |
|---|---|---|---|
| 5,399,586 | 3/1995 | Davies et al. | 514/448 |
| 5,767,148 | 7/1998 | Michel et al. | 514/467 |
| 5,780,676 | 7/1998 | Boehm et al. | 562/490 |

FOREIGN PATENT DOCUMENTS 0 658 553  6/1995  European Pat. Off. .

OTHER PUBLICATIONS

J. Biol. Chem., vol. 270, No. 11, 1995, pp. 6022–6029, XP000574946, L. Zhang et al., "Evidence for the involvement of retinoic acid receptor RAR alpha–dependent signalling pathway in the induction of tissue transglutaminase and apoptosis by retinoids."

Leukemia, vol. 8, No. SPL.3, 1994, pp. S83–S84, XP000575616, P.S. Gill et al, "Solid tumor treatment workshop summary".

*Primary Examiner*—Frederick Krass
*Attorney, Agent, or Firm*—Burns, Doane, Swecker & Mathis, L.L.P.

[57] ABSTRACT

The use of a combination of an alpha RAR receptor-specific agonist ligand and a gamma RAR receptor-specific antagonist ligand to reduce the rate of apoptosis is disclosed.

11 Claims, No Drawings

γ-RAR ANTAGONIST LIGAND OR α-RAR AGONIST LIGAND AS AN APOPTOSIS INHIBITOR

This application is a 371 of PCT/FR96/01569, filed Oct. 08, 1996

The present invention relates to the use of particular retinoids in the preparation of a pharmaceutical composition intended to decrease the rate of apoptosis.

Two types of mechanism are involved in the death of cells. The first, which is the classical type, is termed necrosis. Morphologically, necrosis is characterized by swelling of the mitochondria and the cytoplasm and by nuclear distortion, followed by destruction of the cell and its autolysis, with this latter being accompanied by an inflammation phenomenon. Necrosis occurs in a passive and incidental manner. Tissue necrosis is generally due to the cells being subjected to physical trauma or to a chemical poison, for example.

The other form of cell death is termed apoptosis [Kerr, J. F. R. and Wyllie, A. H., Br. J. Cancer, 265, 239 (1972)]; however, contrary to necrosis, apoptosis does not give rise to any inflammation phenomenon. Apoptosis has been reported to be able to take place under a variety of physiological conditions. Apoptosis is a highly selective form of cell suicide which is characterized by readily observable morphological and biochemical phenomena. Thus, events which are observed, in particular, are condensation of the chromatin, which may or may not be associated with endonuclease activity, the formation of apoptotic bodies, and fragmentation of the deoxyribonucleic acid (DNA), due to endonuclease activation, into 180–200 base pair DNA fragments (these fragments can be observed by agarose gel electrophoresis).

Apoptosis can be regarded as being a programmed cell death which is involved in tissue development, differentiation and renewal. It is also thought that the differentiation, growth and maturation of cells are closely linked to apoptosis and that substances which are able to play a role in the differentiation, growth and maturation of cells are also linked to the phenomenon of apoptosis. Thus, in a human being who is in good health, all these phenomena are in equilibrium.

In the medical field, some pathological situations exhibit a modified, if not deregulated, mechanism of apoptosis or a mechanism of apoptosis which does not provide for a deregulation of another biological phenomenon in order to achieve equilibrium. Thus, it has been reported that deliberate modulation of apoptosis, by inducing it or suppressing it, can make it possible to treat a large number of diseases such as diseases which are linked to an inadequate rate of apoptosis, as in the case of cancer, or to autoimmune diseases or allergies, or, on the contrary, diseases which are linked to an excessive rate of apoptosis, as in the cases of the human immunodeficiency virus (HIV) immunodeficiency syndrome, neurodegenerative diseases (Alzheimer's disease) or excessive damage which is induced during myocardial infarction.

To be specific, a large number of inhibitors of apoptosis, such as cycloheximide, cyclosporin and certain interleukins, have already been described.

In the retinoid field, it is known that all-trans retinoic acid is a powerful modulator (i.e. an inhibitor or, on the contrary, a stimulator, depending on the nature of the treated cells) of the differentiation and proliferation of many normal or transformed cell types. For example, retinoic acid inhibits the differentiation of epithelial cells such as epidermal keratinocytes. It also inhibits the proliferation of many transformed cells such as melanoma cells. These effects on proliferation and differentiation can affect one single cell type simultaneously, as in the case, for example, of human promyelocytic cells which are classified as HL-60 cells; thus, it is known that the proliferation of these cells is inhibited by all-trans retinoic acid and that, at the same time, their differentiation into granulocytes and their apoptosis are induced.

It is known, in a general manner, that all-trans retinoic acid acts on the differentiation and proliferation of cells by interacting with nuclear receptors which are termed RARs (Retinoic Acid Receptors) and which are present in the cell nucleus. To date, three subtypes of RAR receptor have been identified, with these subtypes being termed RAR-α, RAR-β and RAR-γ, respectively. After they have bound the ligand (i.e. the all-trans retinoic acid), these receptors interact with specific response elements (RAREs) in the promoter region of genes which are regulated by retinoic acid. In order to bind to the response elements, the RARs form heterodimers with another type of receptors which are known as RXRs. The natural ligand of the RXRs is 9-cis-retinoic acid. The RXRs are regarded as being master regulatory proteins because they interact to form heterodimers, as with the RARs, with other members of the steroid/thyroid receptor superfamily such as the vitamin D3 receptor (VDR), the triiodothyroxine receptor (TR) and the PPARs (Peroxisome Proliferator Activated Receptors). In addition, the RXRs are able to interact with specific response elements (RXRE) in the form of homodimers.

These complex interactions, and the existence of numerous RAR and RXR receptors, which are expressed differently depending on the tissue and the cell type, explain the pleiotropic effects of the retinoids in virtually all cells.

Many synthetic structural analogues of all-trans retinoic acid or 9-cis-retinoic acid, commonly termed "retinoids", have been described in the literature to date. Some of these molecules are able to bind to, and specifically activate, the RARs or, on the other hand, the RXRs. Furthermore, some analogues are able to bind to, and activate a particular RAR receptor subtype (α, β or γ). Finally, other analogues do not exhibit any particular selective activity with regard to these different receptors. In this respect, and by way of example, 9-cis-retinoic acid activates the RARs and the RXRs at one and the same time without any noteworthy selectivity for either of these receptors (nonspecific agonist ligand), whereas all-trans retinoic acid selectively activates the RARs (RAR-specific agonist ligand), with all subtypes being included. In a general manner, and qualitatively, a given substance (or ligand) is said to be specific for a given family of receptors (or, respectively, for a particular receptor of this family) when the said substance exhibits an affinity for all the receptors of this family (or, respectively, for the particular receptor of this family) which is stronger than that which it otherwise exhibits for all the receptors of any other family (or, respectively, for all the other receptors, of this same family or not).

It has been reported that 9-cis-retinoic acid and all-trans retinoic acid are modulators of apoptosis (activator or inhibitor of apoptosis depending, in particular, on the cell type) and that 9-cis-retinoic acid is the more active of these two modulators, which finding can be explained by the fact that 9-cis-retinoic acid activates both the RARs and the RXRs in contrast to all-trans retinoic acid which only activates the RARs.

In view of what has been said previously, it appears to be of interest to find novel modulators of apoptosis.

In this regard, the Applicant has just discovered that agonist ligands which are specific for receptors of the RAR-α type or antagonist ligands which are specific for receptors of the PAR-γ type are excellent inhibitors of apoptosis in different types of cells, more specifically in thymocytes, when this apoptosis has been induced using receptors of the RAR-γ type or T-cell receptors.

Thus, the present invention relates to the use of at least one ligand selected from an agonist ligand which is specific for receptors of the RAR-α type and an antagonist ligand which is specific for receptors of the RAR-γ type in the preparation of a pharmaceutical composition which is intended to decrease the rate of apoptosis in at least one cell population. More specifically, the cell population corresponds to cells in which apoptosis can be regulated by induction and/or inhibition using receptors of the RAR-γ and/or RAR-α type or in which apoptosis can be regulated by induction using T-cell receptors.

The pharmaceutical composition according to the invention comprises a physiologically acceptable medium.

Agonist ligand which is specific for receptors of the RAR-α type is understood, according to the invention, as meaning any agonist ligand which exhibits a dissociation constant for receptors of the RAR-α type which is at least 10 times lower than its dissociation constant for receptors of the RAR-γ type and which induces differentiation of F9 cells.

Antagonist ligand which is specific for receptors of the RAR-γ type is understood, according to the invention, as meaning any ligand which exhibits a dissociation constant for receptors of the RAR-γ type which is at least 10 times lower than its dissociation constant for receptors of the RAR-α type and which does not induce differentiation of F9 cells.

Thus, it is known that all-trans retinoic acid and certain of its analogues are able to induce differentiation of mouse embryonic teratocarcinoma cells (F9 cells); they are therefore regarded as being agonists for RAR receptors. The secretion of the plasminogen activator which accompanies this differentiation is an index of the biological response of the F9 cells to the retinoids (Skin pharmacol. 1990; 3: pp. 256–267).

The dissociation constants are determined by means of tests which are standard for the skilled person. These tests are described, in particular, in the following references: (1) "Selective Synthetic Ligands for Nuclear Retinoic Acid Receptor Subtypes" in RETINOIDS, Progress in Research and Clinical Applications, Chapter 19 (pp. 261–267), Marcel Dekker Inc, edited by Maria A. Livrea and Lester Packer; (2) "Synthetic Retinoids: Receptor Selectivity and Biological Activity" in Pharmacol Skin, Basel, Karger, 1993, Volume 5, pp. 117–127; (3) "Selective Synthetic Ligands for Human Nuclear Retinoic Acid Receptors" in Skin Pharmacology, 1992, Vol. 5, pp. 57–6; (4) "Identification of Synthetic Retinoids with Selectivity for Human Nuclear Retinoic Acid Receptor-γ" in Biochemical and Biophysical Research Communications, Vol. 186, No. 2, July 1992, pp. 977–983; (5) "Selective High Affinity RAR-α or RAR-β Retinoic Acid Receptor Ligands" in Mol. Pharmacol., Vol. 40, pp. 556–562.

Other characteristics, aspects, aims and advantages of the invention will appear even more clearly from reading the description which follows as well as the various specific examples, which are intended as being illustrative but in no way limiting.

Agonist ligands which are specific for receptors of the RAR-α type and which may, in particular, be mentioned are 4-((5,6,7,3-tetrahydro-5,5,8,8-tetramethyl-2-naphthalenyl) carboxamido)benzoic acid, 4-((5,6,7,8-tetrahydro-5,5,8,8-tetramethyl-2-naphthalenyl)carbamoyl)benzoic acid and 2-hydroxy-4-( 5,5,8,8-tetramethyl-5,6,7,8-tetrahydronaphthalene-2-carboxamido)benzoic acid.

Of the agonist ligands which are specific for receptors of the RAR-α type, preference is given, in the present invention, to using at least one agonist ligand which exhibits a dissociation constant for receptors of the RAR-α type which is at least 20 times lower than its dissociation constant for receptors of the RAR-γ type, such as 4-((5,6,7,8-tetrahydro-5,5,8,8-tetramethyl-2-naphthalenyl) carboxamido)benzoic acid and 2-hydroxy-4-(5,5,8,8-tetramethyl-5,6,7,8-tetrahydronaphthalene-2-carboxamido) benzoic acid.

Antagonist ligands which are specific for receptors of the RAR-γ type and which may, in particular, be mentioned are 2-hydroxy-4-[7-(1-adamantyl)-6-benzyloxy-2-naphthyl] benzoic acid, 2-hydroxy-4-[7-(1-adamantyl)-6-hexyloxy-2-naphthyl]benzoic acid, 4-[7-(1-adamantyl)-6-methoxyethoxymethoxy-2-naphthyl]benzoic acid, 5-[7-(1-adamantyl)-6-benzyloxy-2-naphthyl]-2-thiophenecarboxylic acid, 4-[7-(l-adamantyl)-6-benzyloxy-2-naphthyl]benzoic acid, 4-[7-(1-adamantyl)-6-benzyloxycarbonyl-2-naphthyl]benzoic acid, 2-hydroxy-4-[7-(1-adamantyl)-6-(4-fluorobenzyl)oxy-2-naphthyl] benzoic acid, 4-[7-(1-adamantyl)-6-heptyloxy-2-naphthyl] benzoic acid, 6-[7-(1-adamantyl)-6-methoxyethoxymethoxy-2-naphthyl]nicotinic acid, 2-hydroxy-4-[7-(1-adamantyl)-6-methoxyethoxymethoxy-2-naphthyl]benzoic acid, 2-chloro-4-[7-(1-adamantyl-6-methoxyethoxymethoxy-2-naphthyl]benzoic acid, 4-[7-(1-adamantyl)-6-methoxybutyloxy-2-naphthyl]benzoic acid, 4-[7-(1-adamantyl)-6-methoxymethoxypropyl-2-naphthyl] benzoic acid, 4-[7-(1-adamantyl)-6-methoxyethoxypropyl-2-naphthyl]benzoic acid and 4-[7-(1-adamantyl)-6-acetyloxybutoxy-2-naphathyl]benzoic acid.

Of the antagonist ligands which are specific for receptors of the RAR-γ type, preference is given, in the present invention, to using at least one antagonist ligand which exhibits a dissociation constant for receptors of the RAR-γ type which is at least 20 times lower than its dissociation constant for receptors of the RAR-α type, such as 4-[7-(1-adamantyl)-6-methoxyethoxymethoxy-2-naphthyl]benzoic acid.

Thus, it will be possible to use the pharmaceutical composition according to the invention when it is necessary to decrease the rate of apoptosis in the case of at least one cell population. More specifically, the cell population corresponds to cells in which apoptosis can be regulated by induction and/or inhibition using receptors of the RAR-γ and/or RAR-α type or in which apoptosis can be regulated by induction using T-cell receptors, and therefore, in particular, in cell populations in which receptors of the RAR-γ and/or RAR-α type, or T-cell receptors, are present, such as, for example, in cells which derive from the thymus, in which these three types of receptor are present.

A decrease in the rate of apoptosis can prove to be necessary when there is, therefore, an excessive rate of apoptosis, with this excessive rate resulting from genetic or acquired conditions which are exhibited by the individual to whom it is desired to administer the pharmaceutical composition. These genetic or acquired conditions favour the accumulation of signals which induce apoptosis or lower the threshold at which these signals induce apoptosis.

Diseases or disorders which are linked to an excessive rate of apoptosis and which may be mentioned, more specifically, are the human immunodeficiency virus (HIV)

immunodeficiency syndrome, neurodegenerative diseases, myelodysplastic syndromes (such as aplastic anaemia), ischaemic syndromes (such as myocardial infarction), liver diseases which are induced by toxins (such as alcohol), alopecia, damage to the skin due to UV light, lichen planus, atrophy of the skin, cataract or else graft rejections.

Thus, neurodegenerative diseases which may be mentioned, more specifically, are Azheimer's disease, Parkinson's disease, amyotrophic lateral sclerosis and other diseases linked to degeneration of the brain, such as Creutzfeld-Jakob disease.

The composition according to the invention may be administered by the enteral, parenteral, topical or ocular route. Preferably, the pharmaceutical composition is packaged in a form which is suitable for administration by the systemic route (for injection or perfusion).

For administration by the enteral route, the composition, more specifically the pharmaceutical composition, may be in the forms of tablets, hard gelatin capsules, coated tablets, syrups, suspensions, solutions, powders, granules, emulsions, microspheres or nanospheres, or lipid or polymeric vesicles which permit a controlled release. For administration by the parenteral route, the composition may be in the form of solutions or suspensions for perfusion or injection.

The ligands which are selected from agonist ligands which are specific for receptors of the RAR-α type and antagonist ligands which are specific for receptors of the RAR-γ type and which are used in accordance with the invention are generally administered in a daily dose of from about 0.01 mg/kg to 100 mg/kg of body weight, which is given in one administration or in up to three separate administrations.

When administered by the topical route, the pharmaceutical composition according to the invention is more specifically intended for treating the skin and the mucous membranes and may be present in the form of ointments, creams, milks, pomades, powders, imbibed buffers, solutions, gels, sprays, lotions or suspensions. It can also be in the form of microspheres or nanospheres, or lipid or polymeric vesicles or polymeric patches and hydrogels which permit a controlled release. When administered by the topical route, this composition may be either in anhydrous form or in aqueous form.

When administered by the ocular route, the composition is chiefly in the form of eye lotions.

The ligands which are selected from agonist ligands which are specific for receptors of the RAR-α type and antagonist ligands which are specific for receptors of the RAR-γ type are used, when administered by the topical or ocular route, at a concentration which is generally between 0.001% and 10% by weight, preferably between 0.1 and 1% by weight, based on the total weight of the composition.

The compositions as previously described may, of course, additionally comprise inert or even pharmacodynamically active additives or combinations of these additives, and in particular: wetting agents, depigmenting agents such as hydroquinone, azelaic acid, caffeic acid or kojic acid; emollients; moisturizing agents such as glycerol, PEG 400, thiamorpholinone and its derivatives, or even urea; antiseborrhoeic agents or anti-acne agents, such as S-carboxymethylcysteine, S-benzylcysteamine, and their salts or their derivatives, or benzoyl peroxide; antifungal agents such as ketoconazole or the polymethylene-4,5-isothiazolidin-3-ones; antibacterial agents, carotenoids and, in particular, β-carotene; antipsoriatic agents such as anthralin and its derivatives; and, finally, eicosa-5,8,11,14-tetraynoic and eicosa-5,8,11-trynoic acids, their esters and amides.

These compositions may also comprise flavour-improving agents, preservatives such as the esters of parahydroxybenzoic acid, stabilizing agents, moisture-regulating agents, pH-regulating agents, agents for modifying the osmotic pressure, emulsifying agents, UV-A and UV-B filters, antioxidants, such as a-tocopherol, butylhydroxyanisole or butylhydroxytoluene.

Naturally, the skilled person will see to it that the possible compound(s) to be added to these compositions is/are selected such that the advantageous properties which are attached intrinsically to the present invention are not altered, or are not substantially altered, by the addition which is envisaged.

Several examples which are intended to illustrate the present invention, but which are in no way limiting, will now be given.

EXAMPLE 1

This example demonstrates the in-vitro efficacy of an RAR-γ-specific antagonist ligand as an inhibitor of apoptosis when the apoptosis has been induced by other retinoids.

Culture and preparation of the cells

Thymus glands from untreated 4-week old NMRI male mice (sold by LATI, Gödöllo, Hungary) are used as the starting material for preparing thymocyte suspensions. The medium employed is Sigma RPMI 1640 medium which is supplemented with Gibco foetal calf serum, 2 mM glutamine, 100 IU of penicillin and 100 µg of streptomycin/ml. The thymocytes are then washed and diluted, in order to obtain a final concentration of $10^7$ cells/ml, before incubating them at 37° C. in a humidified incubator under an atmosphere of 5% $CO_2$ and 95% air. The death of the cells is measured by the uptake of trypan blue.

Qualitative and quantitative DNA analysis

The thymocytes are incubated in 24 wells together with various compounds to be tested. After 6 hours of incubation, 0.8 ml volumes of cell suspensions were lysed by the addition of 0.7 ml of lysis buffer containing 0.5% (v/v) Triton X-100, 10 mM Tris, 20 mM EDTA, pH 8.0, before being centrifuged at 13,000 g for 15 minutes.

Quantitative analysis of the DNA: the DNA contained in the supernatant (the fragments) and the pellet (intact chromatin) was precipitated with an equivalent quantity of 10% trichloroacetic acid, resuspended in 5% trichloroacetic acid and then quantified using the diphenylamine reagent (Burton, K. (1956) Biochem. J., 62, 315–322).

Qualitative analysis of the DNA: in parallel, the supernatant was precipitated overnight in ethanol containing 0.15 mM NaCl. The pellets are redissolved in a buffer containing 10 mM Tris, 1 mM EDTA, pH 8.0, after which the solutions are treated with RNase and sequentially extracted with an equal volume of phenol and chloroform/isoamyl alcohol (24/1); the DNA is then precipitated in ethanol before electrophoresis for 3 hours at 60 V in a 1.8% agarose gel. The DNA fragments were then visualized by UV after the gel had been stained with ethidium bromide. The gels obtained display the picture of a ladder of DNA fragments which are multiples of from 180 to 200 base pairs and which are typical for an apoptosis induction. Throughout the experiments, the degree of fragmentation correlates with the number of cells which are dead and which are positive to the trypan blue test.

The results of the quantitative analysis are collected in Table 1 below.

TABLE 1

| Compounds | RAR-α Kd | RAR-γ Kd | Quantities (nM) | % of DNA fragments |
|---|---|---|---|---|
| ATRA | 15.5 | 3 | 5000 | 17 |
| 9-cisRA | 7 | 17 | 1000 | 19 |
| CD437 | 6500 | 77 | 300 | 24 |
| CD2665 | >2253 | 110 | 200 | 0.5 |
| CD2665 + ATRA | — | — | 200 / 5000 | 0 |
| CD2665 + 9-cisRA | — | — | 200 / 1000 | 1.5 |
| CD2665 + CD437 | — | — | 200 / 300 | 1.0 |

ATRA is all-trans retinoic acid
9-cisRA is 9-cis-retinoic acid
CD437 is 6-3-(1-adamantyl)-4-hydroxyphenyl)-2-naphthanoic acid,
CD2665 is 4-[7-(1-adamantyl)-6-methoxyethoxymethoxy-2-naphthyl]benzoic acid The percentage of DNA fragment in this table corresponds to the difference between the percentage of DNA fragment obtained in the treated thymocytes and the percentage of DNA fragment obtained in the untreated thymocytes (basal rate of apoptosis for these thymocytes).

This table demonstrates clearly that apoptosis induced by ATRA, 9-cisRA and CD437 is inhibited by CD2665, which is an antagonist ligand which is specific for receptors of the RAR-γ type.

EXAMPLE 2

This example demonstrates the in-vitro efficacy of an RAR-α-specific agonist ligand as an inhibitor of apoptosis when the apoptosis has been induced by another retinoid.

The procedure is the same as in the preceding example, except that the nature of the ligands to be tested, and their concentration, are altered.

Thus, CD437 (6-3-(1-adamantyl)-4-hydroxyphenyl)-2-naphthanoic acid) (at one single concentration) is incubated with the thymocytes in the presence of different concentrations of CD336 (4-((5,6,7,8-tetrahydro-5,5,8,8-tetramethyl-2-naphthalenyl)carboxamido)benzoic acid).

Table 2 below assembles the results which were obtained.

TABLE 2

| PRODUCTS | QUANTITIES (M) | % of DNA fragments |
|---|---|---|
| CD437 alone | $0.3 \times 10^{-6}$ | 17 |
| CD336 alone | $10^{-8}$ | 0 |
|  | $10^{-7}$ | 0 |
|  | $10^{-6}$ | 0 |
| CD437 + CD336 | CD336:$10^{-8}$ | 17 |
|  | CD336:$10^{-7}$ | 5 |
|  | CD336:$10^{-6}$ | 0 |

The percentage of DNA fragment in this table corresponds to the difference between the percentage of DNA fragment obtained in the treated thymocytes and the percentage of DNA fragment obtained in the untreated thymocytes (basal rate of apoptosis for these thymocytes).

Thus, this table clearly demonstrates that the apoptosis which is induced by CD437, which is an agonist ligand which is specific for receptors of the RAR-γ type, is inhibited in a dose-dependent manner by CD336, which is an agonist ligand which is specific for receptors of the RAR-α type.

EXAMPLE 3

This example demonstrates the in-vitro efficacy of an RAR-α-specific agonist ligand as an inhibitor of apoptosis when the apoptosis has been induced by activating a T-cell receptor The procedure is the same as in Example 1 except that the nature of the compounds to be tested, and their concentration, are changed.

It is known that T cells differentiate into mature T lymphocytes in the thymus. During this differentiation, the T cells proliferate and generate receptors for T cells. The cells which express potentially autoreactive cell receptors, and which interact with cells presenting an antigen undergo apoptosis (negative selection) (Smith et al. (1989) Nature 337, 181–184). This selection can be mimicked in vitro by stimulating the CD3 molecule which is associated with a receptor for T cells by means of adding phorbol dibutyrate and a Ca++ ionophore simultaneously (Iseki et al. (1991) J. Immunol. 147, 4286–4292).

Thus, phorbol dibutyrate (5 ng/ml) and a Ca++ ionophore (0.5 μM) are incubated with thymocytes in the absence or presence of different concentrations of CD336 (4-((5,6,7,8-tetrahydro-5,5,8,8-tetramethyl-2-naphthalenyl) carboxamido)benzoic acid).

The results obtained are assembled in Table 3 below.

TABLE 3

| PRODUCTS | QUANTITIES (nM) | % of DNA fragments |
|---|---|---|
| P + C alone | — | 17 |
| CD336 alone | 30 | 0 |
|  | 300 | 0 |
|  | 3000 | 0 |
| (P + C) + CD336 | CD336:30 | 9.6 |
|  | CD336:300 | 8.4 |
|  | CD336:3000 | 1.1 |

P + C denotes phorbol dibutyrate (5 ng/ml) and a Ca++ ionophore (0.5 μM)

The percentage of DNA fragment in this table corresponds to the difference between the percentage of DNA fragment obtained in treated thymocytes and the percentage of DNA fragment obtained in untreated thymocytes (basal rate of apoptosis for these thymocytes).

Thus, this table clearly demonstrates that the apoptosis which is induced by P+C is inhibited in a dose-dependent manner by CD336, which is an agonist ligand which is specific for receptors of the RAR-α type.

EXAMPLE 4

This experiment demonstrates the in-vivo efficacy of an RAR-γ-specific antagonist ligand as an inhibitor of apoptosis when the apoptosis has been induced by an RAR-γ-specific agonist ligand.

4-week-old male NMRI mice (sold by LATI, Gödöllo, Hungary) were used. In order to induce apoptosis in the thymus, these male mice were treated by a single intraperitoneal injection with 0.5 mg of 6-3-(1-adamantyl)-4-hydroxyphenyl)-2-naphthanoic acid, which was dissolved in 40 μl of DMSO and 0.5 ml of 20% ethanol. In order to see the inhibitory effect of apoptosis which was induced in the thymus by an agonist ligand which was specific for RAR-γ, male mice were treated by a single intraperitoneal injection with a mixture of 0.5 mg of 6-3-(1-adamantyl)-4-hydroxyphenyl)-2-naphthanoic acid (CD437) and 5 mg of 4-[7-(1-adamantyl)-6-methoxyethoxymethoxy-2-naphthyl] benzoic acid (CD2665), with this mixture having been dissolved in 40 μl of DMSO and 0.5 ml of 20% ethanol. For the control, male mice were treated by a single intraperitoneal injection of a mixture of 40 μl of DMSO and 0.5 ml of 20% ethanol. The CD2665 was also tested alone under the same conditions as before and in a quantity of 0.5 mg.

The weight of the thymus was determined after 48 hours of treatment, and the results are assembled in Table 4 below.

TABLE 4

| Treatment | Weight of the thymus (mg) | General state of the animal |
| --- | --- | --- |
| Control | 98.2 ± 19.6 | normal |
| CD437 (0.5 mg) | 31.3 ± 13.6 | normal |
| CD2665 (0.5 mg) | 107.6 ± 21.7 | normal |
| CD437 (0.5 mg) + CD2665 (5 mg) | 63.3 ± 9.1 | normal |

Thus, involution of the thymus is observed after treatment with CD437 alone and no significant change is observed with CD2665, whereas the combination of CD2665 and CD437 results in an involution of the thymus which is much less marked than that observed with CD437 alone.

What is claimed is:

1. A method for decreasing the rate of apoptosis in at least one cell population experiencing same, comprising administering to said at least one cell population an effective apoptosis-inhibiting amount of at least one agonist ligand specific for RAR-α receptors, and at least one antagonist ligand specific for RAR-γ receptors.

2. The method of claim 1 wherein apoptosis of said cell population is regulated by induction and/or inhibition of RAR-γ receptors and/or RAR-α receptors, or is regulated by induction of T-cell receptors.

3. The method of claim 1 wherein said ligand is a compound which is specific for RAR-γ receptors and is selected from the group consisting of 2-hydroxy-4-[7-(1-adamantyl)-6-benzyloxy-2-naphthyl]benzoic acid, 2-hydroxy-4-[7-(1-adamantyl)-6-hexyloxy-2-naphthyl] benzoic acid, 4-[7-(1-adamantyl)-6-methoxyethoxymethoxy-2-naphthyl]benzoic acid, 5-[7-(1-adamantyl)-6-benzyloxy-2-naphthyl]-2-thiophenecarboxylic acid, 4-[7-(1-adamantyl)-6-benzyloxy-2-naphthyl]benzoic acid, 4-[7-(1-adamantyl)-6-benzyloxycarbonyl-2-naphthyl]benzoic acid, 4-[7-(1-adamantyl)-6-benzyloxycarbonyl-2-naphthyl]benzoic acid, 2-hydroxy-4-[7-(1-adamantyl)-6-(4-fluorobenzyl) oxy-2-naphthyl]benzoic acid, 4-[7-(1-adamantyl)-6-heptyloxy-2-napthyl]benzoic acid, 6-[7-(1-adamantyl)-6-methoxyethoxymethoxy-2-naphthyl]nicotinic acid, 2-hydroxy-4-[7-(1-adamantyl)-6-methoxyethoxymethoxy-2-naphthyl]benzoic acid, 2-chloro-4-[7-(1-adamantyl)-6-methoxyethoxymethoxy-2-naphthyl]benzoic acid, 4-[7-(1-adamantyl)-6-methoxyethoxypropyl-2-naphthyl]benzoic acid and 4-[7-(1-adamantyl)-6-acetyloxybutoxy-2-naphthyl] benzoic acid.

4. The method of claim 1 wherein said antagonist ligand which is specific for RAR-γ receptors exhibits a dissociation constant for said receptors which is at least 20 times lower than the dissociation constant of said ligand for RAR-α receptors.

5. The method of claim 4 wherein said ligand is 4-[7(1-adamantyl)-6-methooxyethoxymethoxy-2-naphthyl]benzoic acid.

6. A method according to claim 1 wherein said agonist ligand which is specific for RAR-α receptors exhibits a dissociation constant for said receptors which is at least 20 times lower than the dissociation constant for RAR-γ receptors.

7. A method according to claim 1 wherein said agonist ligand which is specific RAR-α receptors is selected from 4-((5,6,7,8-tetrahydro- 5,5,8,8-tetramethyl-2-naphthalenyl) carboxamido) benzoic acid and 2-hydroxy-4-(5,5,8,8-tetramethyl-5,6,7,8-tetrahydro-naphthalene-2-carboxamido)-benzoic acid.

8. The method according to claim 1 which comprises treating a disease associated with an excessive rate of apoptosis.

9. A method according to claim 8 wherein said disease is selected from the group consisting of human immunodeficiency virus (HIV) immunodeficiency syndrome, neurodegenerative diseases, myelodysplastic syndromes, ischaemic syndromes, liver diseases induced by toxins, alopecia, damage to the skin by UV light, lichen planus, atrophy of the skin, cataract and graft rejection.

10. The method of claim 9 wherein said neurodegenerative diseases are selected from the group consisting of Azheimer's disease, Parkinson's disease, amyotrophic lateral sclerosis and other diseases which are associated with degeneration of the brain.

11. The method of claim 10 wherein said other disease associated with degeneration of the brain is Creutzfeld-Jakob disease.

* * * * *